US006090372A

United States Patent [19]

Finch et al.

[11] Patent Number: 6,090,372

[45] Date of Patent: Jul. 18, 2000

[54] LIQUID DETERGENT COMPOSITIONS AND PROCESS FOR THEIR PREPARATION

[75] Inventors: Timothy David Finch, Bebington, United Kingdom; Philippus Cornelis van der Hoeven, Vlaardingen, Netherlands; David Alan Reed, Bebington, United Kingdom; Helena Maria de Roo, Vlaardingen, Netherlands; Jonathan Frank Warr, Bebington, United Kingdom

[73] Assignee: Lever Brothers Company, division of Conopco, Inc., New York, N.Y.

[21] Appl. No.: 09/108,665

[22] Filed: Jul. 1, 1998

[30] Foreign Application Priority Data

| | | | |
|---|---|---|---|
| Jul. 15, 1997 | [GB] | United Kingdom | 9714897 |
| Jul. 15, 1997 | [GB] | United Kingdom | 97305260 |

[51] Int. Cl.[7] ..... A61K 7/42

[52] U.S. Cl. ..... 424/59; 424/60; 424/402; 510/276; 510/299; 510/319; 510/320; 510/321; 510/322; 510/323; 510/337; 510/338

[58] Field of Search ..... 424/59, 60, 402; 510/276, 299, 319, 320, 321, 322, 323, 337, 338

[56] References Cited

U.S. PATENT DOCUMENTS

| | | | |
|---|---|---|---|
| 4,788,054 | 11/1988 | Bernhardt et al. | 424/59 |

FOREIGN PATENT DOCUMENTS

| | | |
|---|---|---|
| 523956 | 7/1992 | European Pat. Off. . |
| 728749 | 2/1996 | European Pat. Off. . |
| 92/06172 | of 0000 | WIPO . |
| 96/03369 | of 0000 | WIPO . |

*Primary Examiner*—Michael A. Williamson

[57] ABSTRACT

An aqueous liquid detergent composition is substantially transparent in the absence of opacifier contains a sunscreen together less than 5 wt. % of detergency builder and/or comprises a water-miscible polar organic solvent. The solvent and fluorescer or ultraviolet absorbing agent are mixed together as a premix prior to incorporation in the composition as a whole.

20 Claims, No Drawings

LIQUID DETERGENT COMPOSITIONS AND PROCESS FOR THEIR PREPARATION

TECHNICAL FIELD

The present invention relates to liquid detergent compositions which contain a fluorescer or ultraviolet (UV)-absorbent material. The invention also extends to a process for preparation of these materials.

BACKGROUND OF THE INVENTION

The colour of fabrics can be altered during the laundering process or during wear or use by photo fading.

The fading of coloured fabrics by sunlight during wear, and during drying, is a major problem for consumers. Sun fading of fabrics is of specific concern to consumers because the contrast between exposed and unexposed areas makes it particularly noticeable. e.g. on collars, inside versus outside of garments, and on wrap around garments such as saris.

In addition, and especially important because of health considerations, consumers rely on the use of clothes to protect them from UV light. However, as the light weight clothing worn in hot countries provides little protection from UV light it is frequently and increasingly beneficial to enhance the UV protection given by clothes. These effects can be mitigated by treating the fabrics with a sunscreen, usually applied as one component of a detergent composition used to wash the fabrics. Sunscreens absorb UV radiation. Other materials which absorb UV radiation are fluorescers (sometimes called optical brighteners) which re-emit the absorbed radiation in the visible spectrum. For this reason, many sunscreens are also fluorescers, although it is possible for sunscreens to re-emit outside the visible range.

For example, U.S. Pat. No. 4,788,054 teaches the use of N-phenylphthalisomides as ultraviolet radiation absorbers for cotton, wool, polyester and rayon. Fabric care compositions comprising a water dispersible/water soluble copolymers which prevent photofading are disclosed in EP-A-0 523 956.

WO-A-96/03369 discloses the use of butylated hydroxy toluene for the protection of surfaces from physical and chemical degradation.

Recently, it has been reported (Skin Protection against Ultraviolet Light by Cotton Textiles treated with Optical Brighteners, D. Reiner et al, in Proceedings of the 4th World Surfactants Congress (CESIO, Barcelona, 1996) Vol 1, pp. 264–276) that there is an increasing requirement for skin protection against both UV-A and UV-B sunlight. It was reported that certain optical brighteners were especially suited to endowing garments with sunlight protection capability. On the basis of this observation, new compounds were developed especially for that purpose. These are described and claimed in EP-A-0 728 749 which discloses the preparation and use of sunscreen of the formula (I) as hereinafter defined, in liquid detergent compositions comprising more than 5% by weight of builder salts.

There is, however, a persistent problem that in liquid detergent compositions it is difficult to formulate a composition that mitigates photofading and increases the UV barrier of fabrics, whilst remaining of a transparent appearance (in the absence of opacifier). Sunscreens of general formula (I) are known to produce a hazy or cloudy composition when included in conventional transparent liquid detergent compositions. It has proved difficult to incorporate compounds such as disclosed in EP-A-0 728 749 in a stable fashion in aqueous liquid detergent compositions, particularly those of the isotropic kind, and especially, those containing polymers for soil release or anti-dye transfer, or containing enzyme stabilising systems that contribute to soil removal, without inducing formation of structured phases which cause the composition to become opaque and ultimately, lead to physical instability.

In a first aspect, the present invention provides the solution of formulating liquid detergent compositions in substantially transparent form by incorporating less than 5% by weight of builder salts, based on the weight of the total composition.

In a second aspect, the present invention provides the solution of formulating the liquid detergent compositions in substantially clear form by incorporating a water-miscible polar organic solvent.

In the context of the second aspect of the present invention, it should be noted that European patent application WO 92/06172 discloses formulation of a highly built aqueous liquid detergent containing an optical brightener and a polyhydroxy fatty acid amide, wherein the brightener is added to the detergent composition in admixture with the polyhydroxy fatty acid amide. The compositions disclosed contain mixtures of builders selected from a very wide range, present in at least 10% by weight, usually much more.

DEFINITION OF THE INVENTION

Accordingly the first aspect of the present invention provides a liquid detergent composition comprising:

(a) sunscreen of general formula (I) as hereinafter defined; and (b) less than 5% by weight total of builder salts, wherein the composition is substantially transparent in the absence of opacifier.

In a second aspect, the present invention provides an aqueous liquid detergent composition comprising surfactant material, sunscreen and a water-miscible polar organic solvent, the composition being substantially transparent in the absence of opacifier.

A third aspect of the present invention provides a process of preparing a composition according to the first or second aspect of the present invention, the process comprising forming a premix containing water, at least some of the sunscreen and at least some of the organic solvent to form a premix and effecting admixture of the premix with the other components of the composition. For most practical purposes, the premix will contain substantially all of sunscreen and substantially all of the organic solvent which will be present in the final composition, preferably with at least some of the water.

The invention further relates to the use of any detergent composition according to the first aspect of the present invention to reduce the photofading of coloured fabrics and to enhance the UV barrier provided by fabric.

As used herein, the term "sunscreen" means, in the widest sense, a material which when deposited on the fabric at the use concentration absorbs ultraviolet radiation to at least a measurable extent, whether or not it is also a fluorescer/optical brightener. Preferably it has a molar extinction coefficient of greater than 2000 $mol^{-1}$ $cm^{-1}$.

The sunscreen agent used in the composition according to the second aspect of the invention is preferably one of those materials described in EP-A-728 749 or in the aforementioned article of D. Reiner et al. The materials described in EP-A-728 749 include those having the general formula (I) as hereinafter defined.

In the case of the third aspect of the present invention, the weight ratio of water-miscible polar organic solvent to water in the premix is preferably from 1:9 to 9:1, more preferably from 1:5 to 5:1 and most preferably from 1:2 to 2:1.

By the term "opacifier" what is meant is a material which is added to a composition in order to reduce the transparency of the composition.

DETAILED DESCRIPTION OF THE INVENTION

The compositions of the invention preferably contain detergent-active compounds (surfactants). They may optionally contain hydrotropes, bleaching components, enzymes and other active ingredients to enhance performance and properties. They may also contain a water soluble sunscreen.

The liquid detergent compositions of the present invention are substantially transparent in the absence of opacifier. The transparency of the compositions was determined at ambient temperature by the following method.

The transparency of the liquid detergent compositions was determined at ambient temperature by monitoring the transmission of light through the liquid in 1 cm path length quartz cells on a Perkin Elmer Lambda 16 UV/visible spectrometer.

The instrument was calibrated using double distilled water. Double distilled water was carefully transferred into both reference and sample quartz cells via a Pasteur pipette to avoid the formation of micro bubbles which could interfere with the measurements. The cells were placed in the spectrometer, and the instrument calibrated over the wavelength range 800–850 nm using an automatic programme. The slit width was fixed at 0.25 nm. This set the value for double distilled water to 100% at all wavelengths from 800–850nm. After tipping water from the sample cell, the cell was flushed three times with the experimental sample and refilled therewith using a Pasteur pipette. The transmission of the sample at 820 nm was recorded. This method was adapted for all transparency measurements, the compositions of the present invention typically exhibited a transmission of at least 80%.

Typical transmission values in the range 80 to 99.55 were obtained with examples of the invention. Samples with transmissions of greater than or equal to 80% transmission are considered to be transparent.

It is preferred that the compositions of the present invention exhibit a transparency of 85% transmission, most preferably 85% transmission.

The liquid detergent compositions may be isotropic, or less frequently, anisotropic. The latter is formed in the present of a micro-structure of surfactant molecules within the detergent composition.

Typically the viscosity of the liquid detergent composition 1–10,000 cps, preferably 100–1000 cps.

Sunscreen/Fluorescer/UV Absorbing Agent

As defined above, a "sunscreen" must absorb UV radiation to at least a measurable degree when deposited on a fabric at the use concentration. However, it is preferably a UV absorber with a molar extinction coefficient of greater than 2000 $mol^{-1}cm^{-1}$. Most preferably a sunscreen is a material which absorbs UV in the UVA and UVB region of the spectrum. It is especially preferred if the sunscreen is capable of reducing the transmission of harmful UV rays through fabrics and thus increasing the ultraviolet protection factor of the fabric.

In the context of the first aspect of the present invention, the level of sunscreen is preferably from 0.01 wt % to 5 wt % of the total composition, more preferably from 0.05 wt % to 2.5wt %, most preferably from 0.075wt % to 1 wt %.

In the context of the second aspect of the present invention, the sunscreen is preferably incorporated in an amount of from 0.005% to 0.5% by weight of the total composition, more preferably from 0.05% to 0.2%.

The sunscreens used in the compositions of the first aspect of the present invention and preferably also in those of the second aspect of the invention, have a structure of the general formula (I):

(I)

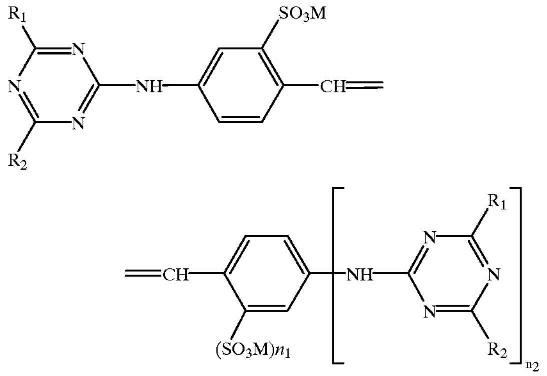

in which M is hydrogen, an alkali metal ion, ammonium or a cation formed from an amine; $R_1$ is a group having one of the following formulae:

(i)

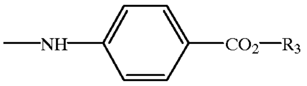

in which $R_3$ is optionally substituted alkyl or optionally substituted aryl;

(ii)

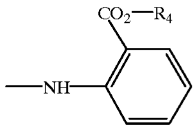

or (iii)

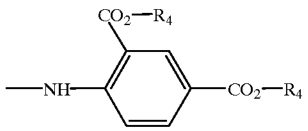

in which $R_4$ is M, optionally substituted alkyl or optionally substituted aryl;

(iv)

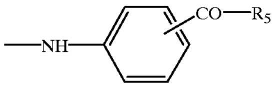

in which $R_5$ is hydrogen, optionally substituted alkyl, optionally substituted aryl or $-NR_7R_8$ in which $R_7$ and $R_8$, independently, are hydrogen, $CH_3$, optionally substituted alkyl or optionally substituted aryl, or $R_7$ and $R_8$ together with the nitrogen atom to which they are attached, form a heterocyclic residue;

(v)

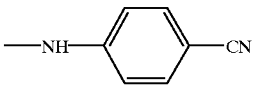

(vi)

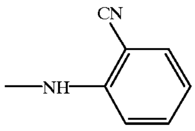

or (vii)

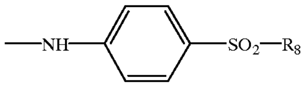

in which $R_8$ is hydrogen, optionally substituted alkyl or optionally substituted aryl, provided that $R_8$ is not carboxymethyl or hydroxymethyl;

$R_2$ is independently hydrogen, optionally substituted alkyl, optionally substituted aryl,

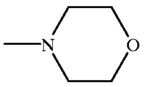

$—OH$, $—NH_2$, $—N(CH_2CH_2OH)_2$, $—N[CH_2CH(OH)CH_3]_2$, $—NH—R_4$, $—N(R_4)_2$ or $—OR_4$, in which $R_4$ has its previous significance; and $n_1$ and $n_2$, independently, are O or 1.

It is especially preferred if the sunscreen is of formula II, formula III or formula IV:

(II)

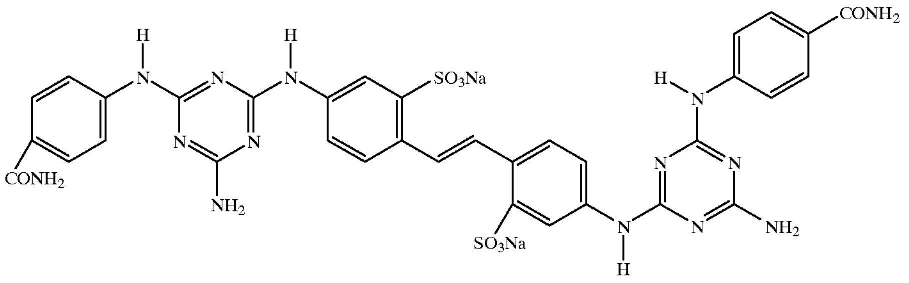

(III)

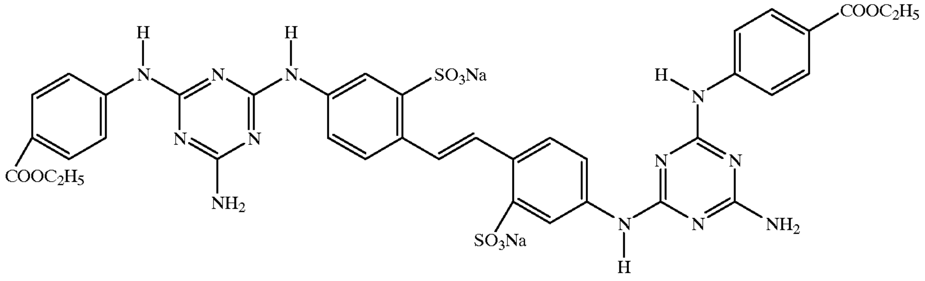

(IV)

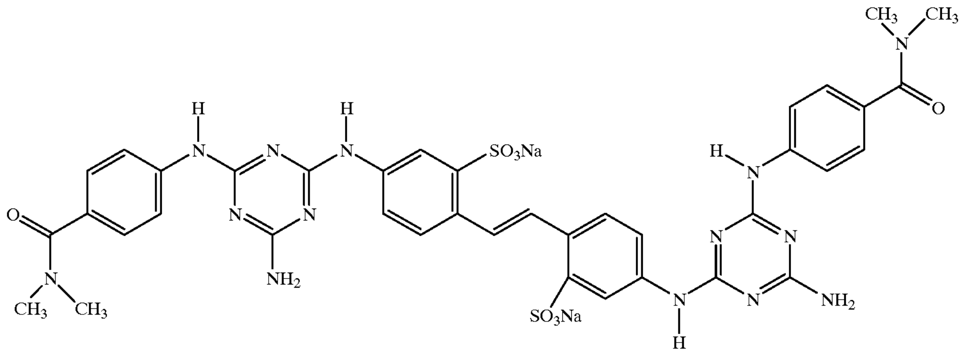

It is believed that the material of formula (IV) is that sold under the Trade Name Tinasorb FD, ex CIBA, which is particularly preferred.

Polar Solvents

Compositions according to the second (and preferably also the first) aspect of the present invention must comprise water-miscible polar organic solvent which is preferably an alcohol such as methanol, ethanol or propanol, or a polyol such as propylene glycol, glycerol, sorbitol or else acetone or mixtures of any of these solvents. It is preferably present from 0.01% to 40% by weight of the total composition, more preferably from 0.05% to 10% and most preferably from 1.0% to 2.5%.

The weight ratio of water-miscible polar organic solvent to water in the premix is preferably from 1:9 to 9:1, more preferably from 1:5 to 5:1 and most preferably from 1:2 to 2:1.

Detergency Builders

The liquid detergent compositions according to the first (and preferably also the second aspect) of the invention contain less than 5% by weight total of builder salts. The total amount of detergency builder in the compositions is preferably less than 4.5 wt %, preferably less than 2.5 wt %. It is especially preferred that the compositions are substantially free from builder salts.

Inorganic builders that may be present within the above total amount include sodium carbonate, if desired in combination with a crystallisation seed for calcium carbonate, as disclosed in GB 1 437 950 (Unilever); crystalline and amorphous aluminosilicates, for example, zeolites as disclosed in GB 1 473 201 (Henkel), or in EPO 384 070 A (Unilever), and mixed crystalline/amorphous aluminosilicates as disclosed in GB 1 470 250 (Procter & Gamble); and layered silicates as disclosed in EP 164 514B (Hoechst). Inorganic phosphate builders, for example, sodium orthophosphate, pyrophosphate and tripolyphosphate may also be present within the above total amount of builder salts.

Organic builders that may be present within the above stated amount of builder include polycarboxylate polymers such as polyacrylates, acrylic/maleic copolymers, and acrylic phosphinates; monomeric polycarboxylates such as citrates, gluconates, oxydisuccinates, glycerol mono-, di- and trisuccinates, carboxymethyloxysuccinates, carboxymethyloxymalonates, dipicolinates, hydroxyethyliminodiacetates, alkyl- and alkenylmalonates and succinates; and sulphonated fatty acid salts. This list is not intended to be exhaustive.

If an organic builder, in the above mentioned amount, is present it is especially preferred if it is a citrate and/ or an acrylic polymer, more especially an acrylic/maleic copolymer.

Builders, both inorganic and organic, present in amounts within the above stated total, are preferably present in alkali metal salt, especially sodium salt, form.

Detergent Active Compounds

The liquid detergent compositions of the invention may contain detergent-active compounds (surfactants) which may be chosen from soap and non-soap anionic, cationic, nonionic, amphoteric and zwitterionic detergent-active compounds, and mixtures thereof. Many suitable detergent-active compounds are available and are fully described in the literature, for example, in "Surface-Active Agents and Detergents", Volumes I and II, by Schwartz, Perry and Berch.

The preferred detergent-active compounds that can be used are soaps and synthetic non-soap anionic and nonionic compounds.

The detergent compositions of the invention preferably contain an anionic surfactant. A preferred anionic surfactant is alkylbenzene sulphonate, particularly linear alkylbenzene sulphonate. Alkylbenzene sulphonates having an alkyl chain length of $C_8$–$C_{15}$ are especially preferred. However, any conventional anionic surfactant may be used.

It is preferred if the level of anionic surfactant is from 5 wt % to 50 wt %, more preferably 10 wt % to 40 wt %, most preferably from 15 wt % to 35 wt %.

Other anionic surfactants suitable for use with the invention are well-known to those skilled in the art. Examples include primary and secondary alkyl sulphates, particularly $C_8$–$C_{15}$ primary alkyl sulphates; alkyl ether sulphates and sulphonates, especially with a $C_8$–$C_{15}$ alkyl chain and four or less ethylene oxide ether groups; paraffin sulphonates, olefin sulphonates; alkyl xylene sulphonates; dialkyl sulphosuccinates; alkyl acyl-N-(hydroxy) alkyl glucamine sulphates, alkyl ester sulphonates and fatty acid ester sulphonates. Sodium salts are generally preferred.

The compositions of the invention may also contain nonionic surfactant.

Nonionic surfactants that may be used include the primary and secondary alcohol ethoxylates, especially the $C_8$–$C_{20}$ aliphatic alcohols ethoxylated with an average of from 1 to 20 moles of ethylene oxide per mole of alcohol, and more especially the $C_{10}$–$C_{15}$ primary and secondary aliphatic alcohols ethoxylated with an average of from 1 to 10 moles of ethylene oxide per mole of alcohol. Non-ethoxylated nonionic surfactants include alkylpolyglycosides, glycerol monoethers, and polyhydroxyamides (glucamide).

It is preferred if the level of nonionic surfactant is from 1 wt % to 35 wt %.

It is preferable if the ratio of anionic surfactant to nonionic surfactant is equal to or greater than 2:3, more preferably greater than or equal to 3:2, most preferably equal to or greater than 4:1.

However, we have found that the problem overcome by the second (and preferably also the first) aspect of the present invention is especially acute with certain combinations of alkylbenzene sulphonate plus alkylether sulphate plus polyalkoxylated nonionic surfactants. This blend may be expressed thus:

when the total amount of alkylbenzene sulphonate anionic surfactant is from 2% to 40% by weight, more especially from 5% to 15% by weight of the total composition, when the total amount of alkylether sulphate anionic surfactant is from 1% to 60%, more especially from 10% to 20% by weight of the total composition; and when the total amount of polyalkoxylated nonionic surfactant is from 2% to 40%, more especially from 5% to 15% by weight of the total composition.

The choice of detergent-active compound (surfactant), and the amount present, will depend on the intended use of the detergent composition. In fabric washing compositions, different surfactant systems may be chosen, as is well known to the skilled formulator, for handwashing products and for products intended for use in different types of washing machine.

If a high foaming product is desired it is preferable to use nonionic surfactants that are not ethoxylated such as cocomonoethanolamide, or which are not highly ethoxylated.

The total amount of surfactant present will also depend on the intended end use and may be as high as 60 wt %, for example, in a composition for washing fabrics by hand. In compositions for machine washing of fabrics, an amount of from 5 to 40 wt % is generally appropriate.

Detergent compositions suitable for use in most automatic fabric washing machines generally contain anionic non-soap surfactant, or nonionic surfactant, or combinations of the two in any ratio, optionally together with small amounts (e.g. from 1% to 2% by weight) of soap.

Counter Ions

Where any component has a counter anion which is not an alkali metal but is a nitrogen containing counter-ion such as monoethanolamine or triethanolamine, then usually it is incorporated at a lower level (e.g. <1% by weight of the composition) as compared to an alkali metal ion.

Enzyme

The compositions of the present invention may suitably comprise one or more enzymes. Suitable enzymes include the proteases, amylases, cellulases, oxidases, peroxidases and lipases usable for incorporation in liquid detergent compositions.

Preferred proteolytic enzymes (proteases) are catalytically active protein materials which degrade or alter protein types of stains when present as in fabric stains in a hydrolysis reaction. They may be of any suitable origin, such as vegetable, animal, bacterial or yeast origin.

Proteolytic enzymes or proteases of various qualities and origins and having activity in various pH ranges of from 4–12 are available and can be used in the instant invention. Examples of suitable proteolytic enzymes are the subtilisins, which are obtained from particular strains of *B. subtilis* and *B. licheniformis,* such as the commercially available subtilisins Maxatase (Trade Mark), as supplied by Gist-Brocades N.V., Delft, Holland, and Alcalase (Trade Mark), as supplied by Novo Industri A/S, Copenhagen, Denmark.

Particularly suitable is a protease obtained from a strain of Bacillus having maximum activity throughout the pH range of 8–12, being commercially available, e.g. from Novo Industri A/S under the registered trade-names Esperase (Trade Mark) and Savinase (Trade-Mark). The preparation of these and analogous enzymes is described in GB 1 243 785. Other commercial proteases are Kazusase (Trade Mark) (obtainable from Showa-Denko of Japan), Optimase (Trade Mark) (from Miles Kali-Chemie, Hannover, West Germany), and Superase (Trade Mark) (obtainable from Pfizer of U.S.A.).

Detergency enzymes are preferably employed in liquid form in amounts of from about 0.1 to about 3.0 wt %. Granular forms of detergency enzymes may be used if they are compatible with the transparent appearance of the liquid detergent composition.

Other Optional Ingredients

The liquid detergent compositions of the present invention may optionally comprise a hydrotrope in a suitable amount.

Suitable hydrotropes include urea and short alkyl chain benzene or xylene sulphonic acids amongst others. Typically the hydrotrope may be present in an amount of 0.1% to 15% by weight.

Other materials that may be present in detergent compositions of the invention (provided that the transparency in the absence of opacifier is not affected) include sodium silicate; lather control agents or lather boosters as appropriate; soil release promoters; anti-dye transfer agents; soil anti-redeposition agents; proteolytic, cellulases lipolytic enzymes; enzyme stabilisers such as borax or alkali metal borates, especially in combination with a polyol such as glycerol or sorbitol; solvents; dyes; perfumes; foam controllers; fabric softening compounds, fluorescers, bleaches and deflocculating polymers. This list is not intended to be exhaustive. Occasionally, such compositions may also contain a bleach or combinations of a bleach and/or fluorescent whitening agent such as those of the Ciba Tinopal family, for example Tinopal CBS-X, Tinopal PLC (DBFBP), Tinopal DCS UNPA-GX, Tinopal 5BM-GX, Tinopal DMS-X or AMS-GX or Tinopal LMS-X or Tinopal SWN or Tinopal SOP or analogous materials from other suppliers.

The composition may contain both at least one ultraviolet absorbing material as claimed in EP-A-0 728 749 (e.g. Tinosorb FD) and one or more conventional optical brighteners, such as those of the DSBP family, i.e. Tinopal CBS-X or those of the stilbene family, i.e. e.g. Tinopal DMS-X, Tinopal AMS-GX, Tinopal TBM-GX and Tinopal UNPA or brighteners of other suppliers with identical structures, and/or cominbations with hydrophobic brighteners such as Tinopal SWN or Tinopal SOP. The weight ratio of total ultraviolet absorbing material to total optical brighteners/fluorescers is preferably from 1:10 to 10:1 and most preferably or typically from 1:2 to 2:1.

Of the foregoing optional materials, polymers for promoting soil release and/or dye transfer inhibition are especially preferred, e.g. PVP or PVP/VI, Sokolan HP22 (ex BASF), TEPA 105 (ex Texaco), modified (e.g. amino-modified) polymethylsiloxanes such as APDMS (ex Rhone Poulenc) or ethoxylated polysiloxanes such as Dimethicone Copolyol 190 (ex Dow Coming), as well as anionic polymers based on sodium carboxymethylcelulose, e.g the Tylose range (ex Hoechst), Narlex H100, Narlex H1200, (ex National Starch) and Alcosperse 725 (ex Alco).

For aesthetic reasons the liquid detergent compositions of the present invention may optionally comprise an opacifier. However, it is an essential feature of the present invention that the compositions are substantially transparent in the absence of an opacifier. Typically, where an opacifier is included, it is present in an amount of from 0.1% to 5% by weight. Suitable opacifiers are well-known in the art and include, for example, polymer latices.

The liquid detergent composition when diluted in the wash liquor (during a typical wash cycle) will give a pH of the wash liquor from 7 to 10.5.

The liquid detergent compositions according to the first (and preferably second) aspects of the present invention are preferably prepared by the method according to the third aspect of the invention. However, in general, they may be prepared by any suitable method, for example, by admixing the essential and optional ingredients thereof in any order to provide transparent liquid compositions (in the absence of opacifier) containing components in the requisite concentrations. Liquid compositions according to the present invention can also be in compact form which means it will contain a lower level of water compared to a conventional liquid detergent. Even if the method according to the third aspect of the invention is not employed, the sunscreen is preferably added at the beginning of the preparation.

The compositions of the present invention are suitable for use as handwashing compositions, machine washing compositions and compositions intended to be applied directly to the substrate to be treated (e.g. in the treatment of curtains, sun hats, window blinds, umberallas, parasols and tents etc.). Also fabric conditioning compositions, in a clear form, may be provided.

The compositions of the present invention are suitable for treating any material or object for which the level of sun protection afforded is required to be improved, but especially for laundry washing.

EXAMPLES

The invention will now be illustrated by the following non-limiting examples. In the examples all percentages are expressed by weight.

Comparative Examples are designated by letters, while Examples of the invention are designated by numbers.

To exemplify the substantially transparent liquid detergent compositions of the present invention the following Examples were prepared,

Example 1

Transparent Liquid Detergent Composition

All the following percentages are expressed by weight in terms of the total composition.

500 g of a 20% by weight surfactant solution containing 16% of sodium alkyl benzene sulphonate*[1] and 4% of $C_{12-15}$ ether sulphate*[2] was prepared by mixing the following ingredients as below:

| % by Weight (active concentration) | Example 1A | Example 1B |
|---|---|---|
| Demineralised Water | Balance | Balance |
| Sunscreen of formula IV*[3] | 0.091 | 0.091 |
| Sodium hydroxide | 2.0 | 2.0 |
| Citric Acid | 0.1 | 0.1 |
| $C_{12}$–$C_{15}$ alkyl ether (3) EO sulphate*[2] | 4.0 | 4.0 |
| Sodium alkyl benzene sulphonic acid*[1] | 14.88 | 14.88 |
| Preservative | 0.016 | 0.016 |
| Perfume | 0.2 | 0.018 |
| Lipase enzyme | — | 0.05 |
| Cellulase enzyme | — | 0.05 |

*[1] Sodium alkyl benzene sulphonate is produced by in-situ neutralisation of the corresponding acid. (Isorchem 113 93% active) $C_{10}$–$C_{13}$ linear alkyl benzene sulphonic acid availble from Enichem.

*[2] available as Dobanol 25-3S-27 from Shell

*[3] available as Tinosorb FD from Giba Geigy (91% active composition)

The components were mixed in the order given above by mechanical stirring using an overhead stirrer. The sunscreen was dissolved in water prior to addition to the composition. Prior to the addition of the preservative and the perfume the pH of the composition was adjusted from approximately pH 2.20 to approximately pH 7.0 by the addition of a small amount of 47% NaOH solution (42° C.). After the addition of all components and mixing was complete the composition was cooled to ambient and the weight of the composition returned to 100% by replacing water lost during preparation with demineralised water.

The compositions were transparent liquid detergent compositions having a pH of approximately 7.4 at ambient temperature.

Example 2

Addition of Builder Salts to Example 1

To samples of the composition of Example 1 additions of different builder salts were made to observe the effect upon the transparency of the compositions. The samples were heated to 45° C. for 2 hours and stored at ambient for 3 days.

The results of the additions are given below:

| | % of Builder Salt Added | | |
|---|---|---|---|
| | 1% | 2% | 3% |
| Sodium tripoly phosphate | Clear | Cloudy | Cloudy |
| Sodium citrate | Clear | Cloudy | Cloudy |
| Sodium carbonate | Cloudy | Cloudy | Cloudy |

This demonstrates the effect of builder salts upon transparent compositions comprising a sunscreen of formula I.

Example 3

| | wt % |
|---|---|
| Nonionic (Synperonic A7) | 9% |
| LBS (Dobanol 25-3-S) | 7% |
| LAS | 4% |
| Fluorescer (Tinosorb FD) | 0.1% |
| Perfume | 0.3% |
| Water | to 100% |

The process steps were as follows:

De-mineralised water was added to the beaker and stirred.

Fluorescer was added and then stirred until partly dissolved. However, the remaining solids dissolved after a few minutes (water at about 20° C.) giving a clear yellow solution. LES (27%) was added and the solution became cloudy. NaOH was next added and the solution became slightly less cloudy and less yellow. Next, the nonionic surfactant was added the solution was warmed to facilitate dissolution. After about 10 minutes with temperature up to about 40° C., the solution became clear and very pale yellow. The LAS was added in acid form slowly and the solution became cloudy again after adding about half the LAS acid. More NaOH was added until the solution became clear. The rest of LAS acid was added and the pH was adjusted to 7, giving a cloudy product. When the pH was increased to 8, the product became totally clear. However, on cooling towards ambient, the product became slightly cloudy again. Perfume was added and the product was allowed to cool to ambient. Heating the product again to about 45° C. gave a clear product which became slightly cloudy again on cooling at about 30° C. The formula can be manipulated to give a totally clear product if required.

Example 4

| | wt % |
|---|---|
| Sorbitol | 2.6% |
| Borax 5aq. | 1.8% |
| Sodium citrate | 1.1% |
| Propylene glycol (PPG) | 2.3% |
| Sodium hydroxide | 0.4% |
| LAS | 3.9% |
| Nonionic surfactant (9EO) | 4.1% |
| LES | 6.9% |
| Tinopal 5BM-GX (optical brightener) | 0.15% |
| Enzymes | 0.75% |

-continued

| | wt % |
|---|---|
| Perfume | 0.1% |
| Tinosorb as 1% solution in PPG/water (1:1) | 0.05% |
| Water | rest |

The process steps were as follows:

Sorbitol/Borax were dissolved in demineralised water. After becoming clear the sodium citrate, propylene glycol and sodium hydroxide were added. Before the Tinopal 5BM-GX, the surfactants were dosed to the alkaline solution, followed by the dosage of the enzymes and the PVP (K15). Tinosorb was dissolved by slow addition under stirring to a mixture of propylene glycol and demineralised water (1:1) to a final concentration of 1%. A volume required to get 0.05% by weight level in the final liquid product was added to the liquid under stirring. Using this method no additional heating was required.

What is claimed is:

1. A liquid detergent composition comprising:

a) a sunscreer having the formula (I);

(I)

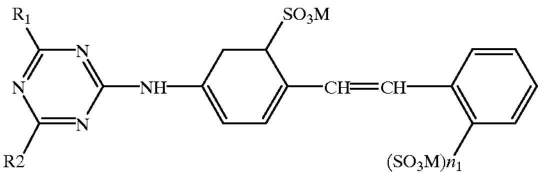

in which:

M is hydrogen, an alkali metal ion, ammonium or a cation formed from an amine;

$R_1$ is a group having one of the following formulae (i) to (vii):

(i)

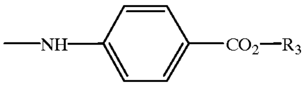

in which $R_3$ is optionally substituted alkyl or optionally substituted aryl;

(ii)

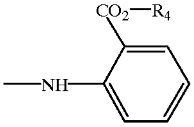

-continued or (iii)

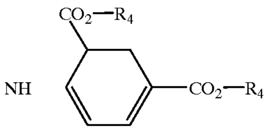

in which $R_4$ is hydrogen, an alkali metal ion, ammonium or cation formed from an amine, optionally substituted alkyl or optionally substituted aryl;

(iv)

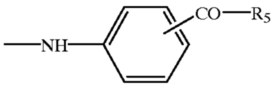

in which $R_5$ is hydrogen, optionally substituted alkyl, optionally substituted aryl or —$NR_7R_8$ in which $R_7$ and $R_8$ independently, are hydrogen, $CH_3$ optionally substituted alkyl or optionally substituted aryl, or $R_7$ and $R_8$, together with the nitrogen atom to which they are attached, form a heterocyclic residue;

(v)

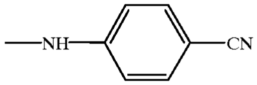

(vi)

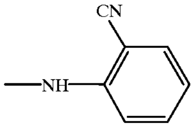

or (vii)

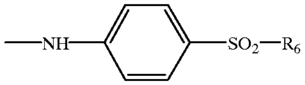

in which $R_6$ is hydrogen, optionally substituted alkyl or optionally substituted aryl, provided that $R_6$ is not carboxymethyl or hydroxymethyl;

$R_2$ is independently hydrogen, optionally substituted alkyl, optionally substituted aryl,

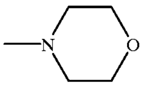

$OH_1$—$NH_2$, —$N(CH_2CH_2OH)_2N(CH_2CH(OH)CH_3)_2$—NH—$R_4$, —$N(R_4)_2$ or —$OR_4$ in which $R_4$ has its previous significance;

$n_1$ and $n_2$, independently, are 0 or 1;

(b) less than 5% by weight total of builder salts; and from 5% to 50% by weight of anionic surfactant;

wherein the composition is substantially transparent in the absence of opacifier.

2. The liquid detergent composition according to claim 1, in which the sunscreen (a), has the formula (II):

(II)

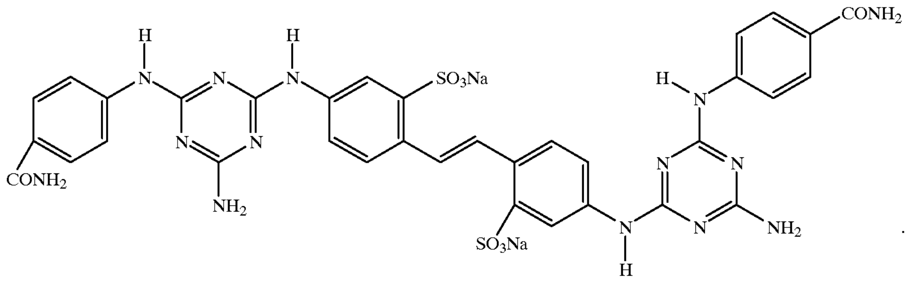

.

3. The liquid detergent composition according to claim 1 in which the sunscreen, (a) has the formula (III):

(III)

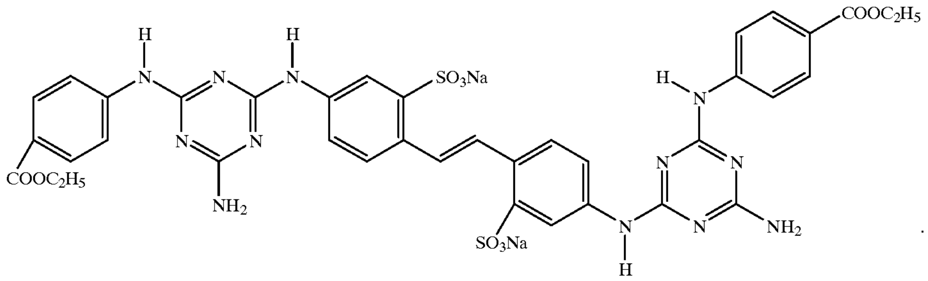

.

4. The liquid detergent composition according to claim 1, in which the sunscreen (a) has the formula IV (IV)

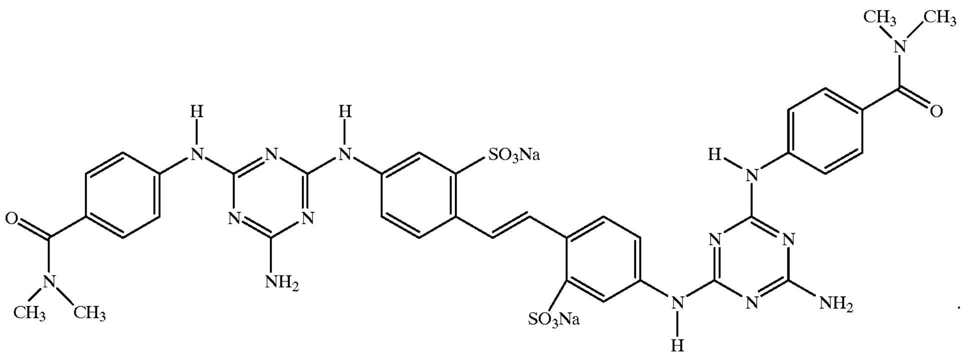

.

5. The liquid detergent composition according to claim 1, in which the level of sunscreen (a) is from 0.01 wt % to 5 wt % of the total composition.

6. The liquid detergent composition according to claim 1, in which the level of builder salts is less than 4.5 wt %.

7. The liquid detergent composition according to claim 6, which are substantially free from builder salts.

8. The liquid detergent composition according to claim 1, which further comprises a hydrotrope.

9. The liquid detergent composition according to claim 8, wherein the hydrotrope is urea.

10. The liquid detergent composition according to claim 1, which further comprises an opacifier.

11. The liquid detergent composition according to claim 1, comprising nonionic and anionic surfactant in which the ratio of anionic surfactant to nonionic surfactant is equal to or greater than 2:3.

12. A liquid detergent composition comprising:

Tinasorb FD having the general formula (IV):

(IV)

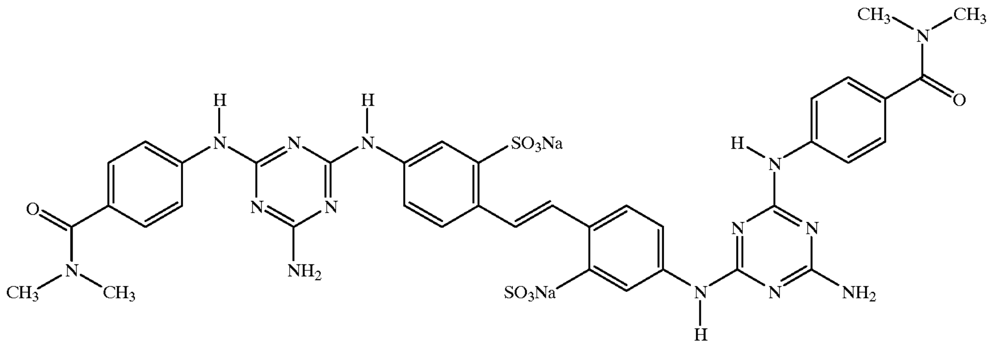

and less than 5% by weight of total builder salts wherein the composition is substantially transparent in the absence of opacifier.

13. An aqueous liquid detergent composition comprising surfactant material a sunscreen and a water-miscible polar organic solvent, wherein the sunscreen has formula (I):

(I)

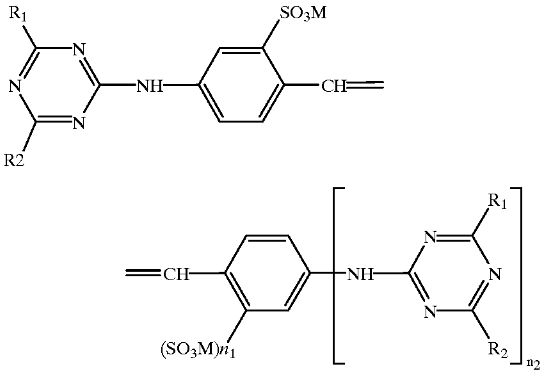

in which:

M is hydrogen, an alkali metal ion, ammonium or a cation formed from an amine;

$R_1$ is a group having one of the following formulae (i) to (vii):

(i)

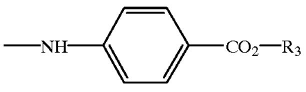

in which $R_3$ is optionally substituted alkyl or optionally substituted aryl;

(ii)

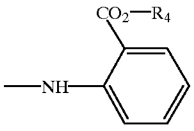

or

-continued (iii)

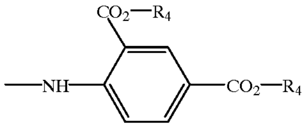

in which $R_4$ is hydrogen, an alkali metal ion, ammonium or cation formed from an amine, optionally substituted alkyl or optionally substituted aryl;

(iv)

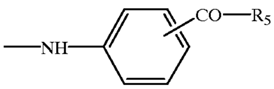

in which $R_5$ is hydrogen, optionally substituted alkyl, optionally substituted aryl or $—NR_7R_8$ in which $R_7$ and $R_8$ independently, are hydrogen, $CH_3$, optionally substituted alkyl or optionally substituted aryl, or $R_7$ and $R_8$, together with the nitrogen atom to which they are attached, form a heterocyclic residue;

(v)

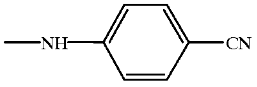

(vi)

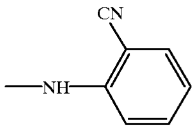

or (vii)

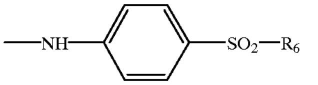

in which $R_6$ is hydrogen, optionally substituted alkyl or optionally substituted aryl, provided that $R_6$ is not carboxymethyl or hydroxymethyl;

$R_2$ is independently hydrogen, optionally substituted alkyl, optionally substituted aryl,

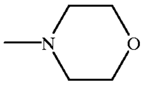

—OH, —$NH_2$, —$N(CH_2CH_2OH)_2$, —$N(CH_2CH(OH)CH_3)_2$, —NH—$R_4$, —$N(R_4)_2$ or —$OR_4$ in which $R_4$ has its previous significance;

$n_1$ and $n_2$, independently, are 0 or 1;

(b) less than 5% by weight total of builder salts; and from 5% to 50% by weight of anionic surfactant;

wherein the composition is substantially transparent in the absence of opacifier.

14. The composition according to claim 13, wherein the total amount of fluorescer and/or ultraviolet absorbing agent is from 0.005% to 0.5% by weight of the total composition.

15. The composition according to claim 14, wherein the water-miscible polar organic solvent is selected from polyols and acetone.

16. The composition according to claim 13, wherein the total amount of water-miscible organic solvent if from 0.01% to 40%, by weight of the total composition.

17. The composition according to claim 13, wherein the surfactant comprises:

from 2% to 40%, by weight of the total composition of the alkylbenzed sulphonate anionic surfactant(s);

from 1% to 60%, by weight of the total composition of the alkylether anionic surfactant(s); and from 2% to 40%, by weight of the total composition of the polyalkoxylated anionic surfactant(s).

18. An-aqueous liquid detergent composition comprising;

surfactant material;

Tinasorb FD having the general formula (IV):

(IV)

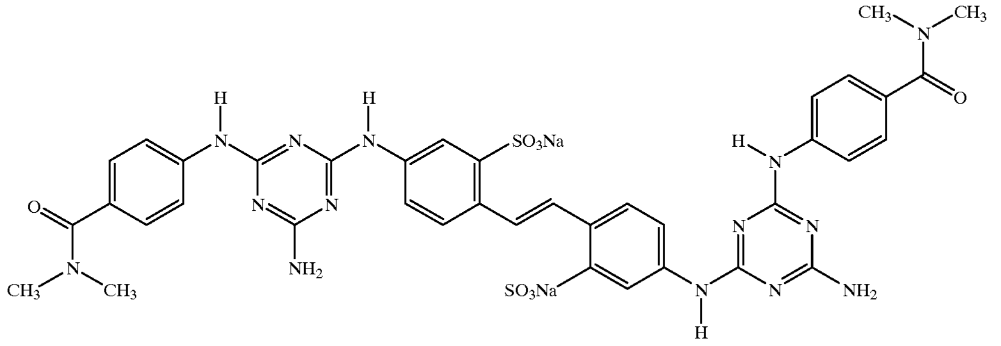

and a water-miscible polar organic solvent, the composition being substantially transparent in the absence of opacifier and comprising less than 5% by weight of builder salts.

19. A process of preparing a composition according to claim 1, which composition comprises a water-miscible polar organic solvent, the process comprising forming a premix containing water, at least some of the fluorescer and at least some of the organic solvent to f orm a premix and effecting admixture of the premix with the other components of the composition.

20. The process according to claim 19, wherein the weight ratio of water-miscible polar organic solvent to water in the premix is from 1:9 to 9:1.

* * * * *

UNITED STATES PATENT AND TRADEMARK OFFICE

CERTIFICATE OF CORRECTION

PATENT NO. : 6,090,372
DATED : July 18, 2000
INVENTOR(S) : Finch et al.

It is certified that error appears in the above-identified patent and that said Letters Patent is hereby corrected as shown below:

Column 13, claim 1,
Line 32, wherein "sunscreer" should have read -- sunscreen --.
and the formula, lines 35, through 40, wherein,

"

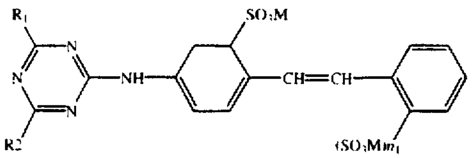

(I)

"

should have read:

--

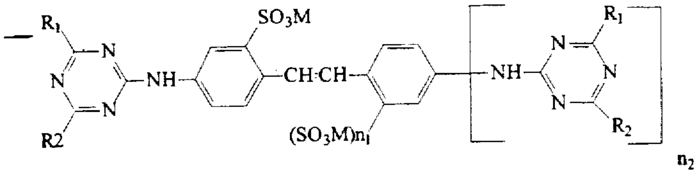

(I)

--

Signed and Sealed this

Twenty-fifth Day of September, 2001

Attest:

*Nicholas P. Godici*

NICHOLAS P. GODICI

*Attesting Officer*

*Acting Director of the United States Patent and Trademark Office*